United States Patent
Liu et al.

(10) Patent No.: US 8,507,250 B2
(45) Date of Patent: Aug. 13, 2013

(54) METHODS AND GENETICALLY ENGINEERED MICRO-ORGANISMS FOR THE COMBINED PRODUCTION OF PDO, BDO AND PHP BY FERMENTATION

(75) Inventors: Dehua Liu, Beijing (CN); Hongjuan Liu, Beijing (CN); Xianjin Ou, Beijing (CN); Yan Sun, Beijing (CN); Yunzhen Xu, Beijing (CN); Yueyong Lei, Yiyang (CN); Weibin Liu, Yiyang (CN)

(73) Assignees: Tsinghua University, Beijing (CN); Hunan Rivers Biotechnology Co. Ltd., Yiyang, Hunan Province (CN)

( * ) Notice: Subject to any disclaimer, the term of this patent is extended or adjusted under 35 U.S.C. 154(b) by 0 days.

(21) Appl. No.: 13/527,933

(22) Filed: Jun. 20, 2012

(65) Prior Publication Data

US 2012/0258521 A1 Oct. 11, 2012

Related U.S. Application Data

(62) Division of application No. 12/620,142, filed on Nov. 17, 2009, now Pat. No. 8,227,217.

(51) Int. Cl.
*C12P 7/42* (2006.01)
*C12P 7/18* (2006.01)
*C12N 9/00* (2006.01)
*C12N 15/00* (2006.01)
*C07H 21/04* (2006.01)

(52) U.S. Cl.
USPC ........ 435/252.3; 435/146; 435/158; 435/183; 435/320.1; 536/23.2

(58) Field of Classification Search
None
See application file for complete search history.

(56) References Cited

FOREIGN PATENT DOCUMENTS

CN 101307336 A 11/2008

OTHER PUBLICATIONS

Jun et al. Appl Biochem Biotechnol. May 2010;161(1-8):491-501.*
Chica et al. Curr Opin Biotechnol. Aug. 2005;16(4):378-84.*
Sen et al. Appl Biochem Biotechnol. Dec. 2007;143(3):212-23.*
Jo et al., "Cloning, expression, and characterization of an aldehyde dehydrogenase from *Escherichia coli* K-12 that utilizes 3-Hydroxypropionaldehyde as a substrate," *Appl Microbiol Biotechnol.*, 81:51-60 (2008).
Yang et al., "Fermentation of 1,3-propanediol by a lactate deficient mutant of *Klebsiella oxytoca* under microaerobic conditions," *Appl Microbiol Biotechnol*, 73(5):1017-1024 (2007).
Kolibachuk et al., "Cloning, Molecular Analysis, and Expression of the Polyhydroxyalkanoic Acid Synthase (*phaC*) Gene from *Chromobacterium violaceum*," *Appl Environ Microbiol.* 65(8):3561-3565 (1999).

* cited by examiner

*Primary Examiner* — Christian Fronda
(74) *Attorney, Agent, or Firm* — Heslin Rothenberg Farley & Mesiti P.C.

(57) ABSTRACT

The present invention relates to genetically engineered micro-organisms for the combined production of 1,3-propanediol (PDO), 2,3-butanediol (BDO), and polyhydroxypropionic acid (PHP) by fermentation. In particular, the invention relates to a genetically engineered micro-organism suitable for combined production of PDO, BDO and PHP by fermentation, characterized in that: compared with corresponding wild-type starting micro-organism, the D-lactate dehydrogenase gene in the genetically engineered micro-organism is deleted or functionally inactivated, and the genetically engineered micro-organism comprises a heterogenous polynucleotide encoding the Coenzyme A-dependent Aldehyde dehydrogenase and a heterogenous polynucleotide encoding the Polyhydroxyalkanoate synthase. Methods for the construction of such micro-organisms, and methods for combined production of PDO, BDO and PHP by fermentation of a genetically engineered bacterium are also taught.

9 Claims, 2 Drawing Sheets

METHODS AND GENETICALLY ENGINEERED MICRO-ORGANISMS FOR THE COMBINED PRODUCTION OF PDO, BDO AND PHP BY FERMENTATION

CROSS REFERENCE TO RELATED APPLICATIONS

This application is a divisional of U.S. patent application Ser. No. 12/620,142, filed Nov. 17, 2009, the disclosure of which is hereby incorporated by reference in its entirety.

FIELD OF INVENTION

The present invention pertains to the field of bio-chemical technology. In particular, the present invention relates to methods for the combined production of 1,3-propanediol (PDO), 2,3-butanediol (BDO), and polyhydroxypropionic acid (PHP) by fermentation as well as genetically engineered micro-organisms useful in such methods and methods for the construction of such micro-organisms.

BACKGROUND OF INVENTION

PDO is an important chemical material which can be used in printing, dyeing, coating, lubricant, and antifreeze industries as an organic solvent. PDO is widely used as monomer in polyester and polyurethane synthesis. Especially, poly(trimethylene terephthalate) (PTT), which is formed by polymerization of PDO with terephthalic acid, has been shown to exhibit superior properties over the polymers formed between terephthalic acid with either 1,2-propanediol, butanediol, or glycol as monomer. Annually, tens of million tons of poly (ethylene terephthalate) (PET) are consumed globally. The chemical stability and biodegradability of PTT are comparable to that of PET, but PTT is superior to PET in some aspects, such as resistance to pollution, ductility and resilience, and anti-UV properties. Furthermore, PTT fiber has advantages of wear resistance, low moisture absorption and low electrostatic generation, making it a potent competitor of Nylon in carpet industry. Additionally, PTT can also be used in the fields of nonwovens, engineering plastics, costume, domestic decoration, padding materials, and wovens. PTT was once selected as one of the six novel petrochemical products in USA in 1998, and therefore regarded as an upgraded product for PET.

The superior properties and commercial value of PTT were recognized as early as 50 years ago. However, since this raw material PDO is hard to produce, which also means a high production cost of PDO, it has been difficult to produce PDO on an industrial scale. So far, only DuPont and Shell could produce PDO by traditional synthesis method from ethylene oxide or propylene, whereas the PDO produced in this way is mainly used by these two companies to produce PTT. This traditional synthesis method suffers from defects of a plurality of undesired byproducts, unsatisfactory selectivity, severe operation conditions of high temperature and high pressure, and huge investment on installations. Further, the raw materials thereof are non-renewable, ethylene oxide is inflammable and explosive, and one of the intermediate material acrolein is extremely toxic. Contrarily, PDO fermentation production method is of great interest recently due to its selectivity and mild operation conditions.

Biosynthetic production of PDO utilizes micro-organisms in which glycerol can be converted into PDO via dismutation. Among the naturally occurring micro-organisms which can convert glycerol into PDO and are mainly anaerobes or facultative anaerobes, *Klebsiella pneumoniae*, *Clostridium butyricum*, and *Citrobacter freundii* show a relatively higher rate of PDO conversion and are more tolerant to glycerol and the product PDO, and thus are promising micro-organisms for future development and application in this area.

BDO, which is a byproduct of the process of fermentation production of PDO, is also an important chemical material. BDO, a colorless, odorless liquid, can be used as fuel or be used to prepare polymers, printing ink, perfume, antifreeze, fumigant, humectant, softening agent, plasticizer, dynamite, and chiral ionophore for pharmaceuticals. BDO may also be used as a valuable chemical material to produce other chemicals. For example, BDO can be converted into methylethylketone via dehydration, which has a wide application, for example, it can be converted into 1,3-butadiene upon further dehydration. BDO can form Styrene by going through Diels-Alder reaction. A condensation reaction occurred between BDO and methylethylketone followed by a hydrogenation reaction results in the production of octane, which is a high quality aviation fuel. A reaction between BDO and acetic acid produces 2,3-butanediol diacetate, which can be used as an additive to improve the flavor of cream. Nonetheless, BDO is generally not isolated and purified during the process of fermentation production of PDO as its yield is relatively low.

Polyhydroxyalkanoates (PHAs) refer to biopolymers generated from β-hydroxy fatty acid monomers via esterification. At least 125 different types of PHA polyester-forming monomer structures have been found, with new monomers being identified continuously. PHAs synthesized in micro-organisms exhibit certain special properties, including biodegradability, biocompatibility, piezoelectricity and optical activities. PHAs are suitable to use in many types of human tissue and organs, e.g., cardiovascular system, cornea, pancreas, gastric-enteric system, kidney, genitourinary system, musculo skeletal system, nervous system, dental and oral tissues, skin, etc. Commercially available PHA products mainly include PHB, PHBV and PHBHHx. Moreover, PHAs can be rigid or soft or flexible, according to the structures and contents of its monomers. PHAs may have many potential applications, on which both basic research and application development studies have been extensively carried out.

The simplest PHA-forming monomer is β-hydroxypropionic acid, and the polymer generated by polymerization of β-hydroxypropionic acid monomers is Polyhydroxypropionic acid (PHP). It has been found that the intensity of PHP is higher than that of other types of PHAs, and thus it may find potential applications in some areas. The monomer directly utilized in the biosynthesis of PHA is β-hydroxy fatty acyl coenzyme A, a form of monomer containing high-energy chemical bond. PHP can be produced by the conversion of intermediate products of glycerol metabolism in micro-organisms (FIG. 1).

In the 1980s, only two PHAs, i.e., PHB (Chemie Linz AG) and PHBV (Zeneca), a co-polymer of hydroxybutyric acid and hydroxyvaleric acid, achieved an industrial scale production. In 1998, a collaborative group from Laboratory of Microbiology, Tsinghua University and Guangdong hangmen Center for Biotech Development Co., Ltd successfully developed a process of industrially producing PHBHHx, a co-polymer of hydroxybutyric acid and hydroxyhexanoic acid, laying a material foundation for the application of this new material.

There are several problems involved in the process of producing PDO by fermentation. For example, at the late stage of fermentation, cell growth arrest, reduced PDO increase, and lactic acid accumulation will generally occur, and a large amount of accumulated lactic acid will make the extraction of PDO more difficult. In addition, the decrease in activity of glycerol dehydrase and insufficiency of intracellular Coenzyme NADH$_2$ at the late stage of fermentation are also the reasons leading to the reduced PDO increase. It is true that higher concentrations of PDO may be achieved by prolonging the course of fermentation, but this will inevitably increase the cost of production. The above issues are the impediments to industrial scale production of PDO. To solve these problems, one of the current strategies is to obtain genetically modified strains which can improve the level of PDO production by fermentation or achieve combined production of other high value-added products, so as to substantially reduce the cost of PDO production.

Currently, efforts on genetic modification of wild-type strains are mainly focused on the following aspects:

(1) To increase the expression of rate-limiting enzymes (e.g., glycerol dehydrase, PDO oxydoreductase) in the reduction pathway by the means of genetic engineering:

Zeng et at [Sun J B., Heuvel J., Soucaille P., Qu Y., and Zeng A. P. Comparative Genomic Analysis of dha Regulon and Related Genes for Anaerobic Glycerol Metabolism in Bacteria. Biotechnol. Prog. 2003 19:263-272] constructed a plasmid containing genes encoding glycerol dehydrase and PDO oxydoreductase and inserted it into a wild-type strain. It was found that the activities of both enzymes in the strain were largely elevated. However, this genetically engineered strain failed to produce higher concentration of PDO during fermentation. By using a new cloning method, HUANG Ribo et at inserted a glycerol dehydrase gene into an *E. coli* strain. It was shown that the resultant strain was capable of producing PDO in a concentration of 30-35 g/L, and the yield of PDO vs. glycerol is about 40% [HUANG Ri-bo et al, *Clostridium perfringen* glycerol dehydrase gene, and its use in 1,3-propylene glycol producing method. Chinese Patent Application No.: 200610019452.X (CN1935991)].

(2) To knockout genes encoding adverse products and block the pathway of by-product metabolism:

ZHANG Yan-ping et at [ZHANG Yan-ping LIU Ming CAO Zhu-an. Construction of *K. pneumoniae* Recombinants of Aldehyde Dehydrogenase Gene Knockout. China Biotechnology, 2005, 25(12):34-38] obtained two recombinant strains by deleting the Aldehyde dehydrogenase (ALDH) gene of ethanol synthesis pathway in *K. pneumoniae* M5aL using homologous recombination technique. The results of batch fermentation experiments under anaerobic conditions showed that yields of ethanol of recombinants were decreased by 43% ~53% and yields of PDO were increased by 27% ~42%, comparing with those of the wild-type *K. pneumoniae* M5aL. But the final concentration of PDO was only 16 g/L. YANG Guang constructed genetically engineered *K. pneumoniae* M5aL strains respectively lacking acetic acid, ethanol and lactic acid metabolism pathways. Although the rate of glycerol conversion was increased, the final concentration and productivity of PDO were decreased [YANG Guang, Molecular Breeding of *Klebsiella pneumoniae* for 1,3-propanediol Production. Beijing: China Agricultural University, 2003 [Thesis]].

(3) To construct Coenzyme regeneration system in PDO producing strains:

HUANG Zhi-hua, et at [HUANG Zhi-hua, ZHANG Yan-ping, CAO Zhu-an. Expression and functional analysis of Formate dehydrogenase in *Klebsiella pneumoniae*. Acta Microbiologica Sinica, 2007, 47 (1): 64-68] isolated a gene from the genome of *C. boidinii* encoding a formate dehydrogenase which is capable of regenerating reduced Coenzyme I (NADH$_2$). They constructed a recombinant plasmid containing the formate dehydrogenase gene, and for the first time constructed a NADH$_2$ regenerating system in a PDO producing strain *K. pneumoniae*. The concentration of 1,3-PDO produced in this *K. pneumoniae* strain transformed with the recombinant plasmid achieved 78.6 g/L, which is 12.5% higher than that of the starting strain YMU2. HUANG Zhi-hua, et at [HUANG Zhi-hua; ZHANG Yan-ping; HUANG Xing; Wang Bao-guang; CAO Zhu-an. Construction of NADH Regeneration System in *Klebisella pneumoniae* with Aldehyde Dehydrogenase Inactivated. China Biotechnology, 2006, 26 (12): 75-80] transformed the recombinant plasmid contaning formate dehydrogenase gene into an Aldehyde dehydrogenase inactivated *Klebsiella pneumoniae* DA 21HB strain. The concentration of PDO produced in this recombinant strain achieved 75.06 g/L, which is 19.2% higher than that of the starting strain DA 21HB.

(4) To construct genetically engineered *E. coli* strains which utilize glucose to produce PDO:

DuPont and Genencor have obtained a number of patents in the field of constructing biocatalysts using glucose as substrate [Bulthuis B A, Gatenby A A, Haynie S L, et al. Method for the Production of Glycerol by Recombinant Organisms. U.S. Pat. No. 6, 358,716, 2002 Jul. 19. Diaz-Torres M, Dunn-Coleman N S, Chase M W, et al. Method for the Recombinant Production of 1,3-Propanediol. U.S. Pat. No. 6,136,576, 2000 Oct. 24. Emptage M, Haynie S L, Laffend L A, et al. Process for the Biological Production of 1,3-Propanediol with High Titer. U.S. Pat. No. 6,514,733, 2003 Aug. 21.], in which an genetically engineered strain with high yields under aerobic conditions was obtained by using *E. coli* K12 as starting strain. This strain was tested in fed-batch fermentation experiments and the concentration of 1,3-PD produced in fermentation is 135 g/L. A drawback of this strain is that it is Coenzyme B$_{12}$ dependent, and thus the production cost is relatively high.

(5) To construct genetically engineered PDO-producing strains from glycerol-producing bacteria:

Cameron et al [Cameron D C, Altaras N E, Hoffman M L et.al. Metabolic Engineering of Propanediol Pathways. Biotechnol. Prog. 1998, 14: 116-125] constructed a *Saccharomyces cerevisia* strain expressing the genes encoding these two enzymes from *Klebsiella pneumoniae*. Fermentation was carried out under anaerobic conditions in a culture medium supplemented with Vitamin B$_{12}$ and containing 5 g/L of glucose as carbon source, but no detectable PDO was found in the broth during 48 hours of fermentation.

SUMMARY OF INVENTION

The object of the invention is to provide a genetically engineered micro-organism suitable for combined production of PDO, BDO and PHP by fermentation and a method of producing PDO, BDO and PHP by fermentation using said micro-organism.

The genetically engineered micro-organism of the invention is derived from a PDO-producing micro-organism from which the gene of D-lactate dehydrogenase has been deleted and into which the Coenzyme A-dependent Aldehyde dehydrogenase gene and Polyhydroxyalkanoate synthase gene have been introduced. The above modifications to the micro-organism result in an increased intracellular synthesis of $NADH_2$, a decreased production of the undesired by-product lactic acid, and an increased yield of the desired by-product BDO.

The invention also relates to a method for combined production of PDO, BDO and PHP by fermentation of a genetically engineered bacterium. As shown in FIG. 2, the method comprises the following steps: (a) constructing a genetically engineered bacterial strain by deleting the D-lactate dehydrogenase gene from a wild-type PDO-producing bacterium and introducing polynucleotides encoding Coenzyme A-dependent Aldehyde dehydrogenase and Polyhydroxyalkanoate synthase into said bacterium; (b) fermenting the bacterial strain by means of fed-batch fermentation with a mixture of glycerol and alkali solution under aerobic conditions; and (c) isolating PDO, BDO and PHP by means of membrane filtration, electrodialysis, concentration, and rectification.

DETAILED DESCRIPTION

Figure 1:
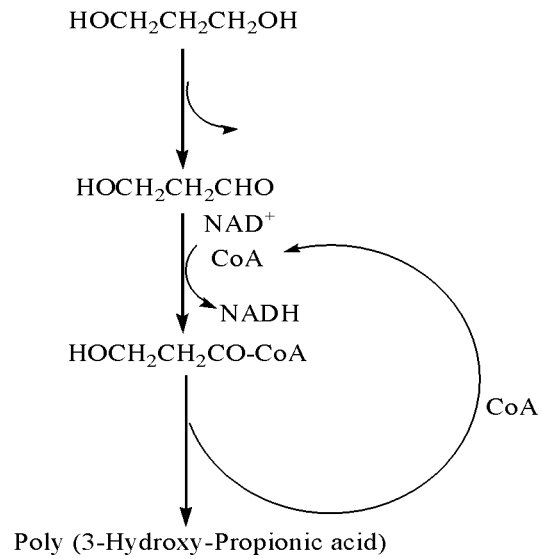
FIG. 1 illustrates PHP in the glycerol metabolism pathway in micro-organisms. $HOCH_2CH_2CH_2OH$ is glycerol, $HOCH_2CH_2CHO$ is 3-Hydroxypropionaldehyde, $HOCH_2CH_2CO$-CoA is 3-hydroxypropionyl coenzyme A, CoA represents Coenzyme A, NAD/NADH represents Coenzyme I.
Figure 2:
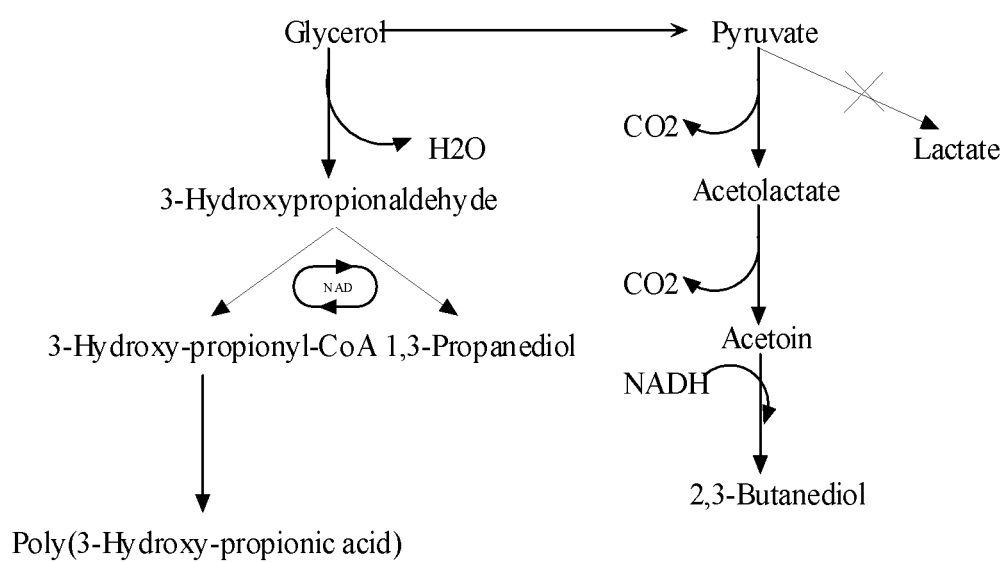
FIG. 2 illustrates the process of producing PHP, PDO and BDO according to the method of the invention.

In one aspect, the present invention provides a genetically engineered micro-organism suitable for combined production of 1,3-propanediol (PDO), 2,3-butanediol (BDO), and polyhydroxypropionic acid (PHP) by fermentation. The genetically engineered micro-organism of the invention is constructed from a wild-type starting micro-organism by deleting or functionally inactivating the D-lactate dehydrogenase gene, and the genetically engineered micro-organism further comprises a heterogenous polynucleotide encoding the Coenzyme A-dependent Aldehyde dehydrogenase and a heterogenous polynucleotide encoding the Polyhydroxyalkanoate synthase. The above modifications to the micro-organism result in an increased intracellular synthesis of $NADH_2$, a decreased production of the undesired by-product lactic acid, and an increased yield of the desired by-product BDO.

With respect to the wild-type starting micro-organism, preferably it is a micro-organism, such as a bacterial strain, capable of producing PDO prior to genetic modification. Preferably, the bacterial strain capable of producing PDO is selected from the group consisting of *Klebsiella* spp, *Citrobacter* spp, *Enterobacter* spp and *Serratia* spp.

The genetic modifications to the micro-organism include deleting the D-lactate dehydrogenase gene from the starting micro-organism, and introducing heterogenous polynucleotides encoding the Coenzyme A-dependent Aldehyde dehydrogenase and the Polyhydroxyalkanoate synthase into the micro-organism.

The heterogenous polynucleotide encoding the Coenzyme A-dependent Aldehyde dehydrogenase can be derived from a bacterium selected from the group consisting of *Klebsiella* spp, *Citrobacter* spp and *Enterobacter* spp, and the heterogenous polynucleotide encoding the Polyhydroxyalkanoate synthase can be derived from *Ralstonia* spp or *Cupriavidus* spp.

The genetic engineering techniques that can be adopted for carrying out the present invention are standard techniques employed in the art, including for example, those described in Sambrook and Russell, Molecular Cloning-a laboratory manual. Cold Spring Harbor Laboratory Press, Cold Spring Harbor, N.Y., USA. Some of these methods are described in Example 1 infra.

In a preferred embodiment, the genetically engineered micro-organism is capable of utilizing glycerol, glycerol broth, crude glycerol by-product of biodiesel industry or crude glycerol by-product of soap industry as substrate for fermentation.

In a further aspect, the present invention provides a method for combined production of 1,3-propanediol (PDO), 2,3-butanediol (BDO), and Polyhydroxypropionic acid (PHP) by fermentation, comprising culturing the genetically engineered micro-organism of the present invention under conditions suitable for the micro-organism to grow and produce PDO, BDO and PHP, and isolating the produced PDO, BDO and PHP.

According to one embodiment, the method of the invention comprises the following steps:

(a) constructing a genetically engineered bacterial strain capable of producing PDO, BDO and PHP by deleting the D-lactate dehydrogenase gene from a wild-type PDO-producing bacterium and introducing polynucleotides encoding the Coenzyme A-dependent Aldehyde dehydrogenase and the Polyhydroxyalkanoate synthase, respectively, into said bacterium;

(b) fermenting the strain by means of fed-batch fermentation, with a mixture of glycerol and alkali solution as the feeding substrate; and (c) isolating PDO, BDO and PHP from the broth by means of membrane filtration, electrodialysis, concentration, and rectification.

To delete the D-lactate dehydrogenase gene in a cell, a genomic DNA sample is isolated and purified from a wild-type PDO-producing strain. The strain may be from *Klebsiella*, *Citrobacter*, or *Enterobacter*. The purified genomic DNA sample is used as template to carry out gene amplification, for example, by PCR using primers designed based on the gene sequence of D-lactate dehydrogenase, to amplify a D-lactate dehydrogenase gene fragment. The amplified D-lactate dehydrogenase gene fragment is then inserted into a cloning vector, such as the pMD18-T vector. The positive cloning vectors are selected and digested, and the amplified gene fragment is recovered and then inserted into a suicidal vector carrying a resistance gene, such as pGPKm or pGP704. The suicidal vector is then transfected into competent host cells, e.g., cells of *E. coli* SM10. Parents exchanging experiments between the host cells containing the recombinant suicidal vector and wild-type host cells will then be carried out to select a strain in which the D-lactate dehydrogenase gene has been deleted, using the resistance gene of the suicidal vector (such as the Kanamycin resistance gene of pGPKm) as the selection marker.

Figure 3:
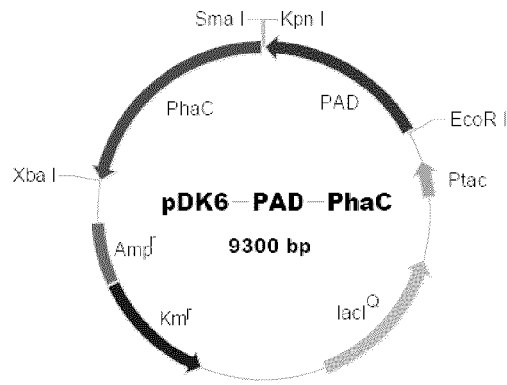
FIG. 3 shows the construction of plasmid PAD_PhaC_pDK6.
Figure 4:
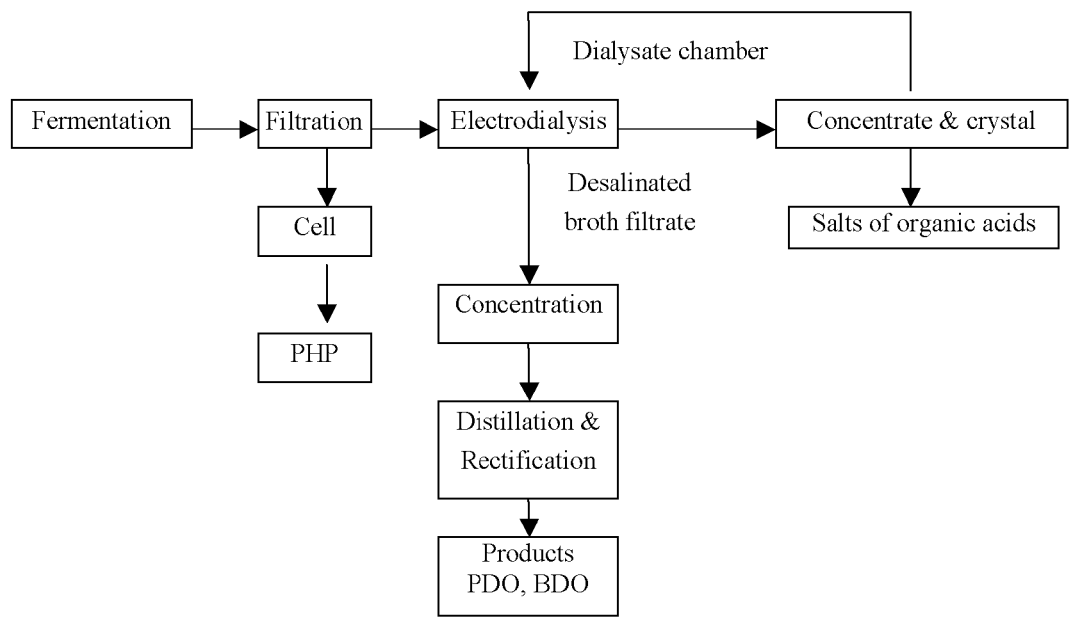
FIG. 4 illustrates the process of isolating PDO, BDO and PHP.

To introduce the polynucleotides encoding the Coenzyme A-dependent Aldehyde dehydrogenase and the Polyhydroxyalkanoate synthase into the strain selected as above, the genomic DNA sample is isolated from a wild-type PDO-producing strain and used as template to clone the gene of Coenzyme A-dependent Aldehyde dehydrogenase (PAD). The strain may be from *Klebsiella*, *Citrobacter*, or *Enterobacter*. The cloned gene of Coenzyme A-dependent Aldehyde dehydrogenase is digested and then inserted into an expression vector, such as pDK6, to construct a first recombinant expression vector, such as PAD_pDK6. And then, the gene of Polyhydroxyalkanoate synthase (PHA synthase, PhaC) which may be derived from *Ralstonia* or *Cupriavidus* is inserted into the first recombinant expression vector, such as PAD_pDK6, to construct a second recombinant expression vector. The construction of an exemplary second recombinant expression vector of this type is shown in FIG. 3, in which the constructed vector is named as PAD PhaC_pDK6. The second recombinant expression vector is then transformed into the competent cells of the strain selected as above in which the gene of D-lactate dehydrogenase has been deleted. Positive clones are identified and isolated as the genetically engineered strains of the present invention.

To carry out the fermentation, the cells of the genetically engineered strain of the invention are first cultured in a solid medium for 16-24 h. The cells are subsequently inoculated into a seed culture medium for culture at 30-37° C. under aerobic conditions, and the culture is then inoculated, at a ratio of 1%-5%, into a fermentation medium with glycerol as the substrate for fermentation at 30-37° C. A fed-batch fermentation is then carried out for 40-60 h at a pH of 5.0-8.0 with glycerol and alkali solution mixed at a ratio of 1:0.05-1.0 as the feeding substrate.

To isolate PDO, BDO and PHP from the fermentation broth, the broth is first subjected to microfiltration and ultrafiltration. The broth filtrate is then desalinated via electrodialysis. The desalinated broth filtrate is then subjected to concentration and rectification to separate the products, PDO and BDO. PHP can be extracted from the cellular remnant separated by filtration. The solution in the dialysate chamber is rich in salts of organic acids, such as sodium succinate hexahydrate, which can also be purified as the by-product through concentration and crystallization.

The wild-type bacterial strains suitable for use in the method of the invention are PDO-producing bacteria of *Klebsiella, Citrobacter, Enterobacter* or *Serratia*. The substrates which used in the fermentation process of the invention include glycerol, glycerol broth, crude glycerol by-product of biodiesel industry or crude glycerol by-product of soap industry.

EFFECTS OF THE INVENTION

The genetically engineered micro-organism of the invention is capable of simultaneously producing PDO, BDO and PHP during fermentation. By using the genetically engineered micro-organism of the invention, the method of the invention shows the following advantages: D-lactic acid is less produced or even absent during fermentation, which may facilitate the isolation of the desired products and reduce the production cost; the BDO and PHP produced will improve the value of the product; the efficiency of raw materials utilization is increased, and the production cost can be lowered. In addition, with the introduction of PHP, the $NADH_2$ content in the micro-organism is significantly increased, which is in favor of PDO production. The present invention can be used in combined production of PDO, BDO and PHP.

The invention will be further illustrated by the following non-limiting examples.

Example 1

1. Construction of genetically engineered bacterial strain
(1) Deletion of the D-lactate dehydrogenase gene Genomic DNA sample was extracted from starting strain *Klebsiella* HR526 (deposited at China General Microbiological Culture Collection Center (CGMCC, Beijing, China) under CGMCC 1.9131), and was subjected to PCR amplification with the following primers:

(SEQ ID NO: 2)
5'-GGAATTCACGGTTGCGAACGGTATGTA-3',
and (SEQ ID NO: 3)
5'-GCTCTAGAAGTGGTCTCCGAAATGCTGA-3'.

The 5'-termini of these two primers contain cleavage sites for EcoRI and XbaI, respectively. The PCR product D-lactate dehydrogenase gene fragment was isolated and sequenced. The sequence of this fragment is shown in SEQ ID NO:1.

The above gene fragment was ligated into cloning vector pMD18-T-vector (TaKaRa). LDH-pMD18-T-vector, the positive cloning vector, was selected and cleaved with both EcoRI and XbaI (TaKaRa). The fragment recovered was then ligated with vector pGPKm (from China Agricultural University), which had been pretreated with the same two enzymes (EcoRI and XbaI). The resultant recombinant plasmid, named as LDH-pGPKm, was then transferred into competent cells of *E. coli* SM10 (from China Agricultural University) by electrotransfection. Parents exchanging experiment was conducted between the *E. coli* SM10 cells containing the recombinant plasmid LDH-pGPKm and the cells of wild-type strain, and a strain in which the D-lactate dehydrogenase gene has been deleted is selected, using the Kanamycin resistance gene of pGPKm as the selection marker.

(2) Insertion of polynucleotides encoding the Coenzyme A-dependent Aldehyde dehydrogenase and the Polyhydroxyalkanoate synthase:

Genomic DNA sample was extracted from starting strain *Klebsiella* HR526 and used as the template to clone the gene of Coenzyme A Dependent Aldehyde dehydrogenase (CoA-Dependent Proionaldehyde Dehydrogenase, PAD) with the following primers:

(SEQ ID NO: 4)
5'-GCTGAATTCATGAATACAGCAGAACTGGA-3',
and (SEQ ID NO: 5)
5'-GGCGGTACCTTAGCGAATGGAAAAACCGT-3'.

The cloned PAD gene (SEQ ID NO:6) was ligated with the vector pDK6 (from China Agricultural University) with the help of EcoRI and KpnI to construct the expression vector PAD_pDK6. A Polyhydroxyalkanoate synthase gene fragment (PhaC) (SEQ ID NO:7) from *Ralstonia eutropha* was digested with Xba I and Hind III (TaKaRa), and ligated with the vector PAD_pDK6 to construct the recombinant vector PAD_PhaC_pDK6. The recombinant vector PAD_PhaC_pDK6 was then transferred into the competent cells of the genetically engineered bacterial strain constructed in step (1) in which the gene of D-lactate dehydrogenase was deleted. A positive clone was isolated and identified and named as strain HR526G.

2. Fermentation (1) Strain: HR526G, which was constructed in Part 1.
(2) Culture Medium: see Table 1.

TABLE 1

The composition of culture medium

| Composition | Seed medium | Fermentation medium |
| --- | --- | --- |
| $(NH_4)_2SO_4$ | 2 g | 4 g |
| $K_2HPO_4 \cdot 3H_2O$ | 3.4 g | 0.69 g |
| $KH_2PO_4$ | 1.3 g | 0.25 g |
| $MgSO_4$ | 0.2 g | 0.2 g |
| Yeast extract | 1 g | 1.5 g |
| glycerol | 30 g | 20-70 g |
| glucose | / | 5-20 g |
| $CaCO_3$ | 1 g | / |
| **Trace element solution | 2.0 ml | 1.0 ml |
| *$Fe^{2+}$ solution | 1.0 ml | 1.0 ml |

*$Fe^{2+}$ solution was prepared by adding 5.0 g $FeSO_4 \cdot H_2O$, 4 ml 37% HCl in 1 liter of water.

(3) Mode of Fermentation:

The cells of the genetically engineered strain were cultured in a solid medium for 16-24 h, and then inoculated into a seed culture medium (250 ml shake flask with 100 ml medium) containing glycerol at a concentration of 30 g/L and cultured for 24 h under aerobic conditions at 30-37° C., 150 rpm. The culture was then inoculated, at a ratio of 5%, into a fermentation medium in a 5 L fermenter with glycerol at an initial concentration of 30 g/L. The fermentation was carried out at 37° C., 150 rpm, pH 6.0, and an aeration of 0.2 vvm, with glycerol and NaOH solution mixed at a ratio of 1:0.1 as the feeding substrate. After 40 h of fermentation, the feeding was stopped.

(4) Results of Fermentation:

After 72 hours, $OD_{650nm}$ achieved 11; the content of PHP was calculated as 1.46% (g/g cell); PDO, 42 g/l; BDO, 14 g/l, no detectable lactic acid was measured.

3. Product Separation

The broth was then subjected to membrane filtration, electrodialysis, concentration, distillation and rectification, and PDO and BDO were obtained. The cellular remnant of filtration was used to extract PHP. The yield of PDO was 85%.

What is claimed is:

1. A genetically engineered micro-organism suitable for combined production of 1,3-propanediol (PDO), 2,3-butanediol (BDO), and polyhydroxypropionic acid (PHP) by fermentation, characterized in that: compared with corresponding wild-type starting micro-organism, the D-lactate dehydrogenase gene in the genetically engineered micro-organism is deleted or functionally inactivated, and the genetically engineered micro-organism comprises a heterogenous polynucleotide encoding the Coenzyme A-dependent Aldehyde dehydrogenase and a heterogenous polynucleotide encoding the Polyhydroxyalkanoate synthase.

2. The micro-organism of claim 1, wherein the wild-type starting micro-organism is capable of producing PDO.

3. The micro-organism of claim 2, wherein the micro-organism is a bacterium.

4. The micro-organism of claim 3, wherein the bacterium is selected from the group consisting of *Klebsiella* spp., *Citrobacter* spp., *Enterobacter* spp., and *Serratia* spp.

5. The micro-organism of claim 4, wherein the D-lactate dehydrogenase gene of the bacterium is deleted.

6. The micro-organism of claim 1, wherein the polynucleotide encoding the Coenzyme A-dependent Aldehyde dehydrogenase is from a bacterium selected from the group consisting of *Klebsiella* spp., *Citrobacter* spp., and *Enterobacter* spp.

7. The micro-organism of claim 1, wherein the polynucleotide encoding the Polyhydroxyalkanoate synthase is from *Ralstonia* spp., or *Cupriavidus* spp.

8. The micro-organism of claim 6, wherein the polynucleotide encoding the Polyhydroxyalkanoate synthase is from *Ralstonia* spp., or *Cupriavidus* spp.

9. The micro-organism of claim 1, wherein the micro-organism is capable of utilizing glycerol, glycerol broth, crude glycerol by-product of biodiesel industry or crude glycerol by-product of soap industry as substrate for fermentation.

* * * * *

SEQUENCE LISTING

<160> NUMBER OF SEQ ID NOS: 7

<210> SEQ ID NO 1
<211> LENGTH: 816
<212> TYPE: DNA
<213> ORGANISM: Klebsiella

<400> SEQUENCE: 1

```
gaattcacgg ttgcgaacgg tatgtatctt cgtcaatgac gacggctgcc gcccggtgct      60
ggaagagctg aaggcccacg gggtgaaata tatcgccctg cgctgcgccg ggtttaacaa     120
cgtcgacctt gaggcggcaa aggagcttgg cctgcgcgtc gtgcgcgttc cagcttactc     180
tccggaagcg gtcgctgagc atgcgatcgg tatgatgatg tcgctcaacc gccgcatcca     240
ccgcgcttac cagcgtaccc gcgatgccaa tttctccctc gaaggcctca ccggcttcac     300
catgtacggc aaaaccgccg gggtgatcgg caccgggaaa attggcgtag cgatgttgcg     360
gatccttaaa ggcttcggca tgcgcctgct ggcgttcgac ccgtacccaa gcgccgccgc     420
gctggagctg ggggtggaat atgttgacct cgccacgctg tacaaggaat cggacgtgat     480
ctccctgcac tgtccgctga ccgacgaaaa ctaccacctg ctcaatcgcg aagccttcga     540
tcagatgaaa gacggggtga tggtgatcaa caccagccgc ggcgccctga tcgactccca     600
ggcggccatc gacgccctga agcaccagaa aattggcgcg ctggggctgg acgtttatga     660
gaacgaacgc gatctgttct ttgaagacaa atccaacgac gtgatccagg acgatgtctt     720
ccgccgcctc tccgcctgcc ataacgtgct gtttaccggc catcaggcgt tcctcaccgc     780
cgaggcgctg atcagcattc ggagaccact tctaga                                816
```

<210> SEQ ID NO 2
<211> LENGTH: 27
<212> TYPE: DNA
<213> ORGANISM: artificial
<220> FEATURE:
<223> OTHER INFORMATION: primer

<400> SEQUENCE: 2

```
ggaattcacg gttgcgaacg gtatgta                                           27
```

-continued

```
<210> SEQ ID NO 3
<211> LENGTH: 28
<212> TYPE: DNA
<213> ORGANISM: artificial
<220> FEATURE:
<223> OTHER INFORMATION: primer

<400> SEQUENCE: 3
gctctagaag tggtctccga aatgctga                                          28

<210> SEQ ID NO 4
<211> LENGTH: 29
<212> TYPE: DNA
<213> ORGANISM: artificial
<220> FEATURE:
<223> OTHER INFORMATION: primer

<400> SEQUENCE: 4
gctgaattca tgaatacagc agaactgga                                         29

<210> SEQ ID NO 5
<211> LENGTH: 29
<212> TYPE: DNA
<213> ORGANISM: artificial
<220> FEATURE:
<223> OTHER INFORMATION: primer

<400> SEQUENCE: 5
ggcggtacct tagcgaatgg aaaaaccgt                                         29

<210> SEQ ID NO 6
<211> LENGTH: 1389
<212> TYPE: DNA
<213> ORGANISM: Klebsiella

<400> SEQUENCE: 6
atgaatacag cagaactgga aacccttatc cgcaccatcc tcagtgaaaa gctcgcgccg        60 acgcccctg cccctcagca agagcagggc atttttctgcg atgtcggcag cgccatcgac       120
gccgctcatc aggcttttct ccgctatcag cagtgtccgc taaaaacccg cagcgccatt       180
atcagcgccc tgcgggagac gctggccccc gagctggcga cgttggcgga agagagcgcc       240
acggaaaccg gcatgggcaa caaagaagat aaatatctga aaaataaagc cgctcttgaa       300
aatacgccgg gcatagagga tctcactacc agcgccctca ccggcgatgg cgggatggtg       360
ctgtttgagt actcgccgtt cggggttatt ggcgccgtgg cgcccagcac caacccaacg       420
gaaaccatta tcaacaacag tatcagcatg ctggcggcgg gtaacagcgt ctatttcagc       480
ccccatcccg gcgcgaaaaa ggtctcgttg aagcttatcg ccaggatcga agagatcgcc       540
taccgctgca gcgggatccg taacctggtg gtgaccgttg ccgagccgac ctttgaagcc       600
acccagcaaa tgatgtccca cccgctgatt gccgttctgg ctatcaccgg tggccctggc       660
attgtggcga tgggcatgaa aagcggtaaa aaagtgatcg gcgctggcgc cggcaatccg       720
ccgtgcatcg ttgatgaaac cgccgatctc gtcaaagccg ccgaagatat catcagcggc       780
gccgccttcg attacaacct gccctgtatc gccgaaaaaa gcctgatcgt cgtcgcctcc       840
gtcgctgacc gcctgatcca gcagatgcag gattttgacg cgctgctgtt gagccgacag       900
gaggccgata ccctgcgtgc cgtctgcctg cccgacggcg cggcgaataa aaaactggtc       960
ggtaaaagcc cggctgcgct gctggcggcg cgggtctcg ccgttccgcc tcgccccct      1020 cgcctgctga tagccgaggt ggaggcgaac gaccctgggg tgacctgcga gcagctgatg      1080
```

```
ccggtgctgc cgatcgtcag ggtcgccgac tttgacagcg ccctggcgct ggccctgcgc    1140
gttgaggagg gtctgcacca caccgccatt atgcactcgc agaatgtctc gcggctcaat    1200
ctggcggcac gcaccctgca gacctccatt tttgtcaaaa atggcccgtc ttacgcggga    1260
atcggcgtcg gcggcgaagg gtttaccacc ttcaccatcg ccacgccaac cggagaaggc    1320
accacctccg cgcggacgtt cgcccgcctg cggcgctgcg tgttgaccaa cggttttttcc   1380 attcgctaa                                                            1389

<210> SEQ ID NO 7
<211> LENGTH: 1767
<212> TYPE: DNA
<213> ORGANISM: Ralstonia eutropha

<400> SEQUENCE: 7
tgccttggct ttgacgtatc gcccaggcgc gggttcgatt gcgcgatagc gcgcattgcc     60
atagttggcg ggcgcggcgc gtttcgcgcc ggcctgcccg ccagccatg cggtccagtc    120 cggccaccag ctgccgtgat gctcgatggc gccggccagc cattgctgcg cgactccgg    180 cagcgcatcg ttagtccagt ggctgcgctt gttcttggcc ggcgggttga tcacaccggc    240
gatatggccc gacgcaccca gcacgaagcg cagcttgttc gccagcagcg cggtcgaggc    300
ataggccgcg gtccacggca cgatatggtc ttcgcgcgag ccgtagatat aggtcggcac    360
gtcgatgctg gccaggtcca ccggcacgcc gcacacggtc agcttgcccg gtaccttgag    420
ctcgttctgc aggtaggtgt ggcgcaggta ccagcagtac cacggccccg gcaggttggt    480
ggcgtcgccg ttccagaaca gcaggtcgaa cggcaccggc gtgttgccct tcaggtagtt    540
gtcgaccacg tagttccaca ccaggtcgtt cgggcgcaag aacgagaagg tattggccag    600
ctcaaggccg cgcagcagcg cgcacggcgc gccggcgccg ccgcccagcg tggcctcgcg    660
caactgcaca tggcccctcgt cgacaaagac gtcgaggatg cccgtgtcgg caaagtccag    720
cagcgtggtc agcagcgtga cgctggcggc cgggtgctcg ccgcgcgcgg ccagcaccgc    780
cagcgcggtc gagacaatgg tgccgcccac gcagaagccg agcacgttga tcttgtcctg    840
gccgctgatg tcgcgcgcga cttcgatggc gcggatggcc gcgtgctcga tgtagtcgtc    900
ccaggtgctg ccggccatgc tggcgtccgg attgcgccac gacaccagaa acaccgtatg    960
tccctgctcc accacatggc gcaccagcga gctctccggc tgcaggtcca ggatgtagta   1020
cttgttgatg cacggcggca ccatcagcag cgggcgcgcg tgcaccttgt cggtcagcgg   1080
cttgtactgc aacagctgga agtactcgtt ctcgaagacc acgcgccctt cggtcaccgc   1140
gacattgcgg ccgacctcaa acgcgctctc gtcggtctgc gagatcttgc gcgtgtcag    1200 gtcttccatc atgttgcgca cgccggcacg cagcgattcg ccgcccgact cgatcagcag   1260
gcgctgcgcc tcgggattgg tggcaaggaa gttggcgggc gacatcgcat cgacccattg   1320
cgagatcgcg aagcggatgc gctggcgggt cttggcatcg gcctcgacgg catcggccag   1380
ctcggtcaag gcgcgcgcat tgagcaggta gaacgcggca gcgaagcgat atgggaggtt   1440
ggtgcgccat gctcgccgg cgaagcgccg gtcgtcagc ggaccggtgg cctcggcctt    1500
gccctcggcc atggcctgcc acagcgctga gaagtccttc atgtagcgct gctggatatc   1560
acccagctgc gccggcgcga tcttgacgcc tgccagcgca tccaggcccg gaatgccgga   1620
cgcggccgcg tggccgttgc cttcagtgcc ctgccactgg cgggaccatt ccagccatgt   1680
ggctggatcg aatggccccg gcgtgacctt gaatggttgg gacttgcctt cctgcgtgga   1740
agctgccgcg cctttgccgg tcgccat                                       1767
```